(12) United States Patent
Huber et al.

(10) Patent No.: US 6,992,099 B2
(45) Date of Patent: Jan. 31, 2006

(54) CONTROL OF ARTHROPODS IN ANIMALS

(75) Inventors: Scot Kevin Huber, Raleigh, NC (US); David Teh-Wei Chou, Raleigh, NC (US); Stefan Schnatterer, Hattersheim (DE); Henricus Maria Martinus Bastiaans, Raleigh, NC (US)

(73) Assignee: Aventis Cropscience S.A., Lyons (FR)

( * ) Notice: Subject to any disclaimer, the term of this patent is extended or adjusted under 35 U.S.C. 154(b) by 0 days.

(21) Appl. No.: 10/406,491

(22) Filed: Apr. 4, 2003

(65) Prior Publication Data

US 2003/0176466 A1    Sep. 18, 2003

Related U.S. Application Data

(62) Division of application No. 09/727,684, filed on Dec. 4, 2000, now Pat. No. 6,569,886.

(60) Provisional application No. 60/168,658, filed on Dec. 2, 1999.

(51) Int. Cl.
*A61K 31/4152* (2006.01)
*C07D 231/16* (2006.01)
*C07D 231/18* (2006.01)

(52) U.S. Cl. .............. 514/407; 548/366.1; 548/366.7; 514/407

(58) Field of Classification Search ............ 548/366.1, 548/366.7; 514/407
See application file for complete search history.

(56) References Cited

U.S. PATENT DOCUMENTS

| | | | |
|---|---|---|---|
| 4,770,692 A | 9/1988 | Stetter et al. | |
| 4,918,085 A | * 4/1990 | D'Silva et al. | ............. 514/407 |
| 5,047,550 A | * 9/1991 | D'Silva | ................... 548/366.7 |
| 5,079,370 A | * 1/1992 | D'Silva et al. | .......... 548/366.7 |
| 5,082,945 A | 1/1992 | Wakselman et al. | |
| 5,175,176 A | 12/1992 | Sasse et al. | |
| 5,232,940 A | 8/1993 | Hatton et al. | |
| 5,283,337 A | 2/1994 | Wakselman et al. | |

FOREIGN PATENT DOCUMENTS

| | | |
|---|---|---|
| AU | 720952 B | 4/1997 |
| AU | 199855541 B2 | 6/1998 |
| EP | 0249033 A | 12/1987 |
| EP | 0257296 A | 3/1988 |
| EP | 0295117 | 12/1988 |
| EP | 0385809 | 9/1990 |
| EP | 0469357 A | 2/1992 |
| EP | 0846686 A1 | 6/1998 |
| JP | 2000169453 A | 6/2000 |
| WO | 94/21606 | 9/1994 |
| WO | 97/07102 | 2/1997 |
| WO | 97/12521 A | 4/1997 |
| WO | 97/28126 | 8/1997 |
| WO | 98/24767 | 6/1998 |
| WO | 98/28277 | 7/1998 |
| WO | 98/28278 | 7/1998 |
| WO | 98/28279 | 7/1998 |

OTHER PUBLICATIONS

DATABASE Accession No. 133:30728, XP 002172128, Abstrct of JP 2000 169453, published Jun. 20, 2000.
Clavel et al, Reactions of Bromotrifluoromethane and Related Halides, Part 12, Transformation of Disulfides into Perfluoroalkyl Sulfides in the Presence of Sulfoxylate Anion Radical Precursors, *J. Chem. Soc. Perkin Trans. 1*, pp. 3371-3375 (1992), published by Chemical Society, London, Great Britain.

* cited by examiner

*Primary Examiner*—Joseph K. McKane
*Assistant Examiner*—Janet L. Coppins
(74) *Attorney, Agent, or Firm*—Buchanan Ingersoll PC

(57) ABSTRACT

A method of controlling parasites in or on an animal comprising administering to the animal a parasiticidally effective, substantially non-emetic 1-arylpyrazole.

32 Claims, No Drawings

CONTROL OF ARTHROPODS IN ANIMALS

CROSS-REFERENCE TO RELATED APPLICATIONS

This application is a divisional of U.S. patent application Ser. No. 09/727,684, filed Dec. 4, 2000, Now U.S. Pat. No. 6,569,886, which claims the benefit of U.S. Provisional Application No. 60/168,658, filed Dec. 2, 1999, both of which are incorporated by reference herein in their entireties and relied upon.

The present invention relates to a method of control of parasites in animals, compositions comprising a compound effective for the said control and compounds effective against parasites.

It is generally a goal of agronomists and veterinarians to possess sufficient means to control pests, particularly arthropods, when they attempt to invade or attack mammals, particularly domestic animals and/or livestock. A classical method of controlling such pests has been the use of topical and/or systemic pesticides on or in the domestic animal which is being attacked. Generally effective treatments include the oral administration of insect growth regulators, such as lufenuron, or antihelminth compounds such as an ivermectin or an avermectin, or the topical application of the insecticide fipronil. It is advantageous to apply pesticides to animals in oral form so as to prevent the possible contamination of humans or the surrounding environment.

It is an object of the present invention to provide new pesticides which may be used in domestic animals.

Another object of the invention is to provide safer pesticides for domestic animals.

Another object of the invention is to provide new pesticides for domestic animals that may be used in lower doses than existing pesticides.

These objects are met in whole or in part by the present invention.

U.S. Pat. No. 5,079,370, EP-A 0846686, WO 98/24769 and WO 97/28126 disclose the use of arylpyrazoles as parasiticidal agents. However, these references are completely silent on the problem that antiparasitical agents often elicit emesis in the animal to be protected or cured from the parasites.

The present invention provides a method of controlling parasites in or on an animal comprising administering, preferably orally, to the animal a parasiticidally effective, substantially non-emetic amount of a 1-arylpyrazole of formula (I):

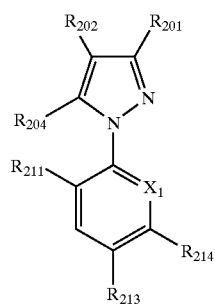

(I)

wherein:

$R_{201}$ is cyano, C(O)alkyl, C(S)NH$_2$, C(NH)OR$_{203}$, C(NH)SR$_{203}$, alkyl, C(=NOH)NH$_2$, C(=NNH$_2$)NH$_2$, C(O)NH$_2$, C(O)NHR$_{205}$, C(O)NR$_{205}$R$_{206}$, haloalkyl or heterocyclyl from the group:

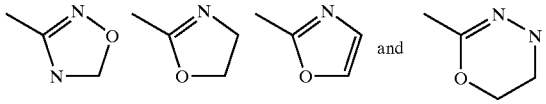

optionally substituted by $R_{203}$;

$R_{202}$ is S(O)$_h$R$_{203}$, C$_2$–C$_6$ alkenyl, C$_2$–C$_6$ haloalkenyl, cycloalkyl, halocycloalkyl, cycloalkyl-alkyl, C$_2$–C$_6$ alkynyl, nitro or imidazol-2-yl optionally substituted by alkyl, alkoxy, haloalkyl, halogen, cyano and/or nitro;

$R_{203}$ is alkyl or haloalkyl;

$R_{204}$ is —OH, R$_{205}$O—, HC(O)O—, R$_{205}$C(O)O—, R$_{205}$OC(O)O—, NH$_2$C(O)O—, R$_{205}$NHC(O)O—, R$_{205}$R$_{206}$NC(O)O—, R$_{205}$S(O)$_n$C(O)O—, R$_{206}$SO$_2$O—, arylSO$_2$O—, (C$_4$–C$_7$)-oxacycloalkyloxy, R$_{205}$R$_{206}$N—C(NR$_{205}$)—O—, R$_{205}$R$_{206}$N—C(NH)—O—, R$_{205}$NH—C(NR$_{205}$)—O—, R$_{205}$NH—C(NH)—O—, R$_{205}$N=CH—O—, R$_{205}$N=C(R$_{206}$)—O—, R$_{205}$NH—C(S)—O—, R$_{205}$R$_{206}$N—C(S)—O—;

$R_{205}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, hetaryl optionally substituted, arylalkyl optionally substituted, hetarylalkyl optionally substituted, C$_2$–C$_6$ alkenyl, C$_2$–C$_6$ alkynyl;

$R_{206}$ is alkyl, haloalkyl, cycloalkyl, halocycloalkyl, alkoxyalkyl, haloalkoxyalkyl, aryl optionally substituted, hetaryl optionally substituted, arylalkyl optionally substituted, hetarylalkyl optionally substituted;

or $R_{205}$ and $R_{206}$ may form together with the nitrogen to which they are attached a 3 to 7 membered ring which additionally may contain one or more heteroatoms selected from nitrogen, oxygen and sulfur;

$X_1$ is selected from nitrogen and C—R$_{212}$;

$R_{211}$, $R_{212}$ are independently selected from halogen, hydrogen, CN, C$_1$–C$_3$ alkyl and NO$_2$;

$R_{213}$ is selected from halogen, haloalkyl, haloalkoxy, —S(O)$_k$CF$_3$, and —SF$_5$ or forms a ring with R$_{214}$;

$R_{214}$ is hydrogen or may constitute together with R$_{213}$ a group of OCF$_2$O, CF$_2$OCF$_2$, CF$_2$OCF$_2$O and CF$_2$CF$_2$O, which forms together with the carbons they are attached to a five to six membered ring; and h, k and n are independently selected from 0, 1, and 2;

and veterinarily acceptable salts thereof.

By the term "veterinarily acceptable salts" is meant salts the anions of which are known and accepted in the art for the formation of salts for veterinary use. Suitable acid addition salts, e.g. formed by compounds of formula (I) containing a basic nitrogen atom, e.g. an amino group, include salts with inorganic acids, for example hydrochlorides, sulphates, phosphates and nitrates and salts with organic acids for example acetic acid.

When $R_{204}$ is OH the pyrazole structure can also be exhibited by its tautomeric form as pyrazolon structure.

Unless otherwise specified, alkyl and alkoxy groups are straight chain or branched and are generally lower alkyl and alkoxy groups, that is having from one to six carbon atoms, preferably from one to four carbon atoms. Generally, the haloalkyl, haloalkoxy and haloalkylamino groups have from one to four carbon atoms. Halogen means F, Cl, Br, and I, preferably F and Cl. The haloalkyl and haloalkoxy and haloalkylamino groups can bear one or more halogen atoms; preferred groups of this type include —$CF_3$ and —$OCF_3$. Cycloalkyl groups generally have from 3 to 6 carbon atoms, preferably from 3 to 5 carbon atoms and may be substituted by one or more halogen atoms. Preferably in compounds of formula (I), alkyl groups are generally substituted by from one to five halogen atoms, preferably from one to three halogen atoms. Chlorine and fluorine atoms are preferred.

In compounds of formula (I) the following examples of radicals are provided:
An example of cycloalkylalkyl is cyclopropylmethyl;
an example of cycloalkoxy is cyclopropyloxy; and
an example of alkoxyalkyl is $CH_3OCH_2$—.

Generally, in dialkylamino or di(haloalkyl)amino radicals, the alkyl and haloalkyl groups on nitrogen may be chosen independently of one another.

Generally, the term "aryl" means a carbocyclic aromatic radical having preferably 6 to 14, in particular 6 to 12, carbon atoms, for example phenyl, naphthyl or biphenylyl, preferably phenyl;

the term "heterocyclyl" preferably means a hetaryl or heteroaliphatic ring system, "hetaryl" preferably being understood as meaning an aryl radical in which at least one CH group is replaced by N and/or at least two adjacent CH groups are replaced by S, NH or O, for example a radical of thiophene, furan, pyrrole, thiazole, oxazole, imidazole, isothiazole, isoxazole, pyrazole, 1,3,4-oxadiazole, 1,3,4-thiadiazole, 1,3,4-triazole, 1,2,4-oxadiazole, 1,2,4-thiadiazole, 1,2,4-triazole, 1,2,3-triazole, 1,2,3,4-tetrazole, benzo[b]thiophene, benzo[b]furan, indole, benzo[c]thiophene, benzo[c]furan, isoindole, benzoxazole, benzothiazole, benzimidazole, benzisoxazole, benzisothiazole, benzopyrazole, benzothiadiazole, benzotriazole, dibenzofuran, dibenzothiophene, carbazole, pyridine, pyrazine, pyrimidine, pyridazine, 1,3,5-triazine, 1,2,4-triazine, 1,2,4,5-triazine, quinoline, isoquinoline, quinoxaline, quinazoline, cinnoline, 1,8-naphthyridine, 1,5-naphthyridine, 1,6-naphthyridine, 1,7-naphthyridine, phthalazine, pyridopyrimidine, purine, pteridine or 4H-quinolizine;

and the term "heteroaliphatic ring system" preferably means a ($C_3$–$C_8$)cycloalkyl radical in which at least one carbon unit is replaced by O, S or a group NR' and R' is hydrogen, ($C_1$–$C_4$)alkyl, ($C_1$–$C_4$)alkanoyl, ($C_1$–$C_4$)alkoxycarbonyl, ($C_1$–$C_4$)alkylsulfonyl, ($C_1$–$C_4$)alkoxy or aryl.

The substituents with which the various aliphatic, cycloaliphatic, aromatic and heterocyclic ring systems can be provided are, for example, halogen, nitro, cyano, di-($C_1$–$C_4$)alkylamino, ($C_1$–$C_4$)alkyl, ($C_3$–$C_8$)cycloalkyl, ($C_1$–$C_4$)trialkylsilyl, ($C_1$–$C_4$)alkoxy, ($C_1$–$C_4$)alkoxy-($C_1$–$C_4$)alkyl, ($C_1$–$C_2$)alkoxy-[$CH_2CH_2O$]$_{0,1,2}$-ethoxy, ($C_1$–$C_4$)alkylthio, ($C_1$–$C_4$)alkylsulfinyl, ($C_1$–$C_4$)alkylsulfonyl, phenyl, benzyl, phenoxy, halophenoxy, ($C_1$–$C_4$)alkylphenoxy, ($C_1$–$C_4$)alkoxyphenoxy, phenylthio, heterocyclyl, heterocyclylthio or heterocyclyloxy, it being possible for one or more, in the case of fluorine also up to the maximum number of, hydrogen atoms in the alkyl radicals and the radicals derived therefrom to be replaced by halogen, preferably chlorine or fluorine, where, in the event that these substituents are ($C_1$–$C_4$)alkyl, they may also be linked cyclically and where one or two aliphatic carbon units in these fused ring systems, such as, for example, the indane, di-, tetra- or decahydronaphthyl or benzocycloheptane system, may be replaced by heteroatom units such as oxygen or sulfur and where one or more, in the case of fluorine also up to the maximum number of, hydrogen atoms on the aliphatic carbon atom units can be replaced by halogen or ($C_1$–$C_4$) alkyl.

It is also to be understood that enantiomeric and diastereomeric forms of the compounds of formulae (I) and salts thereof are embraced by the present invention.

By the term non-emetic is meant a compound that does not generally elicit emesis from the animal when a protective, preventative or cleaning dose is administered to the animal. By the term emesis is meant vomiting. Generally an emetic substance elicits the said emesis in less than 24 hours after administration, preferably less than 8 hours, more preferably less than 2 hours. Generally when the compounds of the invention are administered to a population of animals, more than 70% of the animals are free of emesis, preferably more than 80%, most preferably more than 90%.

Preferred compounds of the formula (I) are those wherein:
$R_{201}$ is cyano, C(O)alkyl, C(S)$NH_2$, alkyl, C(=NOH)$NH_2$ or C(=$NNH_2$)$NH_2$;
$R_{202}$ is S(O)$_h$$R_{203}$, $C_2$–$C_3$ alkenyl, $C_2$–$C_3$ haloalkenyl, cycloalkyl, halocycloalkyl, cycloalkyl-alkyl, $C_2$–$C_3$ alkynyl;
$R_{203}$ is alkyl or haloalkyl;
$R_{204}$ is —OH, $R_{205}$O—, HC(O)O—, $R_{205}$C(O)O—, $R_{205}$OC(O)O—, $NH_2$C(O)O—, $R_{205}$NHC(O)O—, $R_{205}$$R_{206}$NC(O)O—, $R_{205}$S(O)$_n$C(O)O—;
$R_{205}$ is alkyl, haloalkyl, cycloalkyl, halocycloalkyl, alkoxyalkyl, haloalkoxyalkyl, aminoalkyl, alkylaminoalkyl, dialkylaminoalkyl, haloalkylaminoalkyl, di(haloalkyl)aminoalkyl,
$R_{206}$ is alkyl, haloalkyl, cycloalkyl, halocycloalkyl, alkoxyalkyl, haloalkoxyalkyl, or $R_{205}$ and $R_{206}$ may form together with the nitrogen to which they are attached a 3 to 7 membered ring which additionally may contain one or more heteroatoms selected from nitrogen, oxygen and sulfur;
$X_1$ is selected from nitrogen and C—$R_{212}$;
$R_{211}$, $R_{212}$ are independently selected from halogen, hydrogen, CN, and $NO_2$;
$R_{213}$ is selected from halogen, haloalkyl, haloalkoxy, —S(O)$_k$$CF_3$, and —$SF_5$
$R_{214}$ is hydrogen; and
h, k and n are independently selected from 0, 1, and 2.

Further compounds of formula (I) which are preferred according to the present invention are those wherein:
$R_{201}$ is cyano;
$R_{202}$ is S(O)$_h$$R_{203}$;
$R_{203}$ is alkyl or haloalkyl;
$R_{204}$ is OH or $R_{205}$O;
$X_1$ is selected from nitrogen and C—$R_{212}$;
$R_{211}$ and $R_{212}$ are independently selected from halogen, hydrogen, CN and $NO_2$;
$R_{213}$ is selected from halogen, haloalkyl, haloalkoxy, —S(O)$_k$$CF_3$, and —$SF_5$; and
h and k are independently selected from 0, 1, and 2.

The compounds of formula (I) of the present invention preferably have one or more of the following features:
$R_{201}$ is cyano;
$R_{203}$ is halomethyl, preferably $CF_3$;
$R_{211}$ and $R_{212}$ are independently halogen;
$X_1$ is C—$R_{212}$;
$R_{213}$ is haloalkyl, haloalkoxy or —$SF_5$; or
h is 0 or 1, or 2.

A further embodiment of the invention includes compounds of the formula (I), with the proviso that if $R_{201}$ is CN and $R_{202}$ is $S(O)_nR_{203}$ then $R_{204}$ is not $R_{205}O$ or $R_{205}R_{206}N$—C(O)—O—.

In another aspect of the present invention there is provided a method of controlling parasites in or on an animal by administering to the animal an 1-arylpyrazole of formula (II):

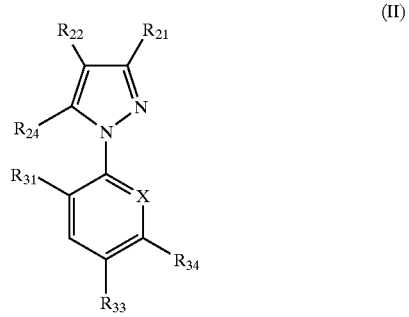

wherein:
$R_{21}$ is cyano, C(=S)NH$_2$, C(=NOH)NH$_2$ or C(=NNH$_2$)NH$_2$;
$R_{22}$ is $S(O)_mR_{23}$;
$R_{23}$ is alkyl or haloalkyl;
$R_{24}$ is OH, HC(O)O—, $R_{25}$C(O)O—, $R_{25}$OC(O)O—, $R_{25}R_{25}$—N—C(O)—O— or $R_{25}$S(O)$_n$C(O)O—;
$R_{25}$ is alkyl, haloalkyl, cycloalkyl, halocycloalkyl, alkoxyalkyl, haloalkoxyalkyl, adamantyl, adamantyl, aminoalkyl, alkylaminoalkyl, dialkylaminoalkyl, haloalkylaminoalkyl, di(haloalkyl)aminoalkyl, aryl optionally substituted, hetaryl optionally substituted, arylalkyl optionally substituted, hetarylalkyl optionally substituted, C$_2$–C$_6$ alkenyl, C$_2$–C$_6$ alkynyl;
or two groups $R_{25}$ may form together with the nitrogen to which they are attached a 3 to 7 membered ring which additionally may contain one or more heteroatoms selected from nitrogen, oxygen and sulfur;
X is selected from nitrogen and C—$R_{32}$;
$R_{31}$ and $R_{32}$ are independently selected from halogen, hydrogen, CN, C$_1$–C$_3$ alkyl and NO$_2$;
$R_{33}$ is selected from halogen, haloalkyl, haloalkoxy, —S(O)$_r$CF$_3$, and —SF$_5$ or forms a ring together with $R_{34}$;
$R_{34}$ is hydrogen or may constitute together with $R_{213}$ a group of OCF$_2$O, CF$_2$OCF$_2$, CF$_2$OCF$_2$O and CF$_2$CF$_2$O, which forms together with the carbons they are attached to a five to six membered ring;
m is 0, 1 or 2;
r is selected from 0, 1, and 2;
and veterinarily acceptable salts thereof;
provided that if $R_{21}$ is cyano then $R_{24}$ is not $R_{25}R_{25}$—N—C(O)—O—.

Preferred are compounds of formula (II), wherein:
$R_{21}$ is cyano, C(=S)NH$_2$, C(=NOH)NH$_2$ or C(=NNH$_2$)NH$_2$;
$R_{22}$ is $S(O)_mR_{23}$;
$R_{23}$ is alkyl or haloalkyl;
$R_{24}$ is OH, HC(O)O—, $R_{25}$C(O)O—, $R_{25}$OC(O)O— or $R_{25}$S(O)$_n$C(O)O—;

$R_{25}$ is alkyl, haloalkyl, cycloalkyl, halocycloalkyl, alkoxyalkyl, haloalkoxyalkyl;
X is selected from nitrogen and C—$R_{32}$;
$R_{31}$ and $R_{32}$ are independently selected from halogen, hydrogen, CN, C$_1$–C$_3$ alkyl and NO$_2$;
$R_{33}$ is selected from halogen, haloalkyl, haloalkoxy, —S(O)$_r$CF$_3$, and —SF$_5$.

In another aspect of the present invention there is provided a compound of formula (II) or salt thereof as hereinbefore described with the proviso that the compound is not 1-(2,6-dichloro-4-trifluoromethylphenyl)-3-cyano-4-trifluoromethylthio-5-hydroxypyrazole.

A further preferred class of compounds of formula (II) are those wherein:
$R_{21}$ is cyano;
$R_{22}$ is $S(O)_mR_{23}$;
$R_{23}$ is haloalkyl, preferably CF$_3$;
$R_{24}$ is OH;
X is selected from nitrogen and C—$R_{32}$;
$R_{31}$ and $R_{32}$ are independently selected from halogen,
$R_{33}$ is selected from halogen, haloalkyl, haloalkoxy, —S(O)$_r$CF$_3$, and —SF$_5$;
m and r are independently selected from 0, 1, and 2 with the proviso that the compound is not 1-(2,6-dichloro-4-trifluoromethylphenyl)-3-cyano-4-trifluoromethylthio-5-hydroxypyrazole.

In a further aspect of the invention the following groups of compounds are provided:
Compounds of the formula (I), wherein
$R_{201}$ is C(O)NH$_2$, C(O)NHR$_{205}$, C(O)NR$_{205}$R$_{206}$, C(O)N=S(R$_{203}$)$_2$, haloalkyl or heterocyclyl from the group:

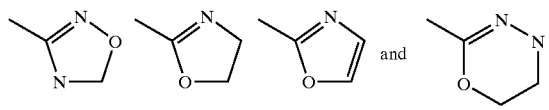

optionally substituted by $R_{203}$;
Compounds of the formula (I), wherein
$R_{202}$ is nitro or imidazol-2-yl optionally substituted by alkyl, alkoxy, haloalkyl, halogen, cyano, nitro;
Compounds of the formula (I), wherein
$R_{204}$ is $R_{206}$SO$_2$O—, aryl-SO$_2$O—, (C$_4$–C$_7$)-oxacycloalkyloxy, $R_{205}$R$_{206}$N—C(NR$_{205}$)—O—, $R_{205}$R$_{206}$N—C(NH)—O—, $R_{205}$NH—C(NR$_{205}$)—O—, $R_{205}$NH—C(NH)—O—, $R_{205}$N=CH—O—, $R_{205}$N=C(R$_{206}$)—O—, $R_{205}$NH—C(S)—O—, $R_{205}$R$_{206}$N—C(S)—O—;
Compounds of the formula (I), wherein
$R_{214}$ constitute together with $R_{213}$ a group of OCF$_2$O, CF$_2$OCF$_2$, CF$_2$OCF$_2$O and CF$_2$CF$_2$O, which forms together with the carbons they are attached to a five to six membered ring.

The compounds 1-(2,6-dichloro-4-trifluoromethylphenyl)-3-cyano-4-trifluromethylsulfinyl-5-hydroxypyrazole and 1-(2,6-dichloro-4-trifluoromethylphenyl)-3-cyano-4-trifluromethylsulfonyl-5-hydroxypyrazole are highly preferred compounds according to the invention.

The following compounds of formula (I) are preferred according to the present invention as listed in Tables 1 to 3. The Compound Numbers are for identification purposes only. The following symbols are hereby defined: Me means methyl; Et means ethyl; n-Pr means n-propyl; i-Pr means isopropyl; n-Bu means n-Butyl; and Ph means Phenyl.

TABLE 1

Compounds of formula (I) wherein $R_{201}$ is cyano; $R_{202}$ is $SCF_3$; $R_{211}$ is Cl, $X_1$ is C—Cl, $R_{214}$ is H and $R_{213}$ is $CF_3$ or $SF_5$.
Phys. data: melting point (° C.) or NMR ($^1$H, $^{19}$F-NMR, ppm)

| Compound Number ($R_{213} = CF_3$) | Compound Number ($R_{213} = SF_5$) | $R_{204}$ | Phys. data |
|---|---|---|---|
| 1-1 | 1-2 | OH | 19F: −44.9 −63.8 |
| 2-1 | 2-2 | OMe | mp. 83 |
| 3-1 | 3-2 | OEt | mp. 105 |
| 4-1 | 4-2 | OPr | |
| 5-1 | 5-2 | O-i-Pr | |
| 6-1 | 6-2 | O-n-Bu | |
| 7-1 | 7-2 | OCH$_2$OMe | |
| 8-1 | 8-2 | OCH$_2$CH$_2$OMe | |
| 9-1 | 9-2 | OCH$_2$OEt | |
| 10-1 | 10-2 | OCH$_2$CH$_2$OEt | |
| 11-1 | 11-2 | OC(O)Me | |
| 12-1 | 12-2 | OC(O)Et | |
| 13-1 | 13-2 | OC(O)n-Pr | |
| 14-1 | 14-2 | OC(O)H | |
| 15-1 | 15-2 | OC(O)NH$_2$ | |
| 16-1 | 16-2 | OC(O)NHMe | |
| 17-1 | 17-2 | OC(O)NHEt | |
| 18-1 | 18-2 | OC(O)NHnPr | |
| 19-1 | 19-2 | OC(O)NMe$_2$ | mp. 126 |

TABLE 2

Compounds of formula (I) wherein $R_{201}$ is cyano; $R_{202}$ is $SOCF_3$; $R_{211}$ is Cl, $X_1$ is C—Cl, $R_{214}$ is H and $R_{213}$ is $CF_3$ or $SF_5$.
Phys. data: melting point (° C.) or NMR ($^1$H, $^{19}$F-NMR, ppm)

| Compound Number ($R_{213} = CF_3$) | Compound Number ($R_{213} = SF_5$) | $R_{204}$ | Phys. data |
|---|---|---|---|
| 1-3 | 1-4 | OH | mp. 185 |
| 2-3 | 2-4 | OMe | mp. 136 |
| 3-3 | 3-4 | OEt | mp. 157 |
| 4-3 | 4-4 | OPr | |
| 5-3 | 5-4 | O-i-Pr | |
| 6-3 | 6-4 | O-n-Bu | |
| 7-3 | 7-4 | OCH$_2$OMe | |
| 8-3 | 8-4 | OCH$_2$CH$_2$OMe | |
| 9-3 | 9-4 | OCH$_2$OEt | |
| 10-3 | 10-4 | OCH$_2$CH$_2$OEt | |
| 11-3 | 11-4 | ONa | 19F: −60.9 −72.6 |
| 12-3 | 12-4 | OC(O)Et | |
| 13-3 | 13-4 | OC(O)n-Pr | |
| 14-3 | 14-4 | OC(O)H | |
| 15-3 | 15-4 | OC(O)NH$_2$ | |
| 16-3 | 16-4 | OC(O)NHMe | |
| 17-3 | 17-4 | OC(O)NHEt | |
| 18-3 | 18-4 | OC(O)NHnPr | |
| 19-3 | 19-4 | OC(O)NMe$_2$ | |

TABLE 3

Compounds of formula (I) wherein $R_{201}$ is cyano; $R_{202}$ is $SO_2CF_3$; $R_{211}$ is Cl, $X_1$ is C—Cl, $R_{214}$ is H and $R_{213}$ is $CF_3$ or $SF_5$.
Phys. data: melting point (° C.) or NMR ($^1$H, $^{19}$F-NMR, ppm)

| Compound Number ($R_{213} = CF_3$) | Compound Number ($R_{213} = SF_5$) | $R_{204}$ | Phys. data |
|---|---|---|---|
| 1-5 | 1-6 | OH | 19F: −63.8 −79.9 |
| 2-5 | 2-6 | OMe | mp. 151 |
| 3-5 | 3-6 | OEt | mp. 132 |
| 4-5 | 4-6 | OPr | |
| 5-5 | 5-6 | O-i-Pr | |
| 6-5 | 6-6 | O-n-Bu | |
| 7-5 | 7-6 | OCH$_2$OMe | |
| 8-5 | 8-6 | OCH$_2$CH$_2$OMe | |
| 9-5 | 9-6 | OCH$_2$OEt | |
| 10-5 | 10-6 | OCH$_2$CH$_2$OEt | |
| 11-5 | 11-6 | OC(O)Me | |
| 12-5 | 12-6 | OC(O)Et | |
| 13-5 | 13-6 | OC(O)n-Pr | |
| 14-5 | 14-6 | OC(O)H | |
| 15-5 | 15-6 | OC(O)NH$_2$ | |
| 16-5 | 16-6 | OC(O)NHMe | |
| 17-5 | 17-6 | OC(O)NHEt | |
| 18-5 | 18-6 | OC(O)NHnPr | |
| 19-5 | 19-6 | OC(O)NMe$_2$ | |

TABLE 4

Compounds of formula (I) wherein $R_{201}$ is alkyl or haloalkyl; $R_{202}$ is $SO_hR_{203}$; $R_{211}$ is Cl, $X_1$ is C—Cl, $R_{214}$ is H and $R_{213}$ is $CF_3$;
Phys. data: melting point (° C.) or NMR ($^1$H, $^{19}$F-NMR, ppm)

| Compound No | $R_{201}$ | $R_{202}$ | $R_{204}$ | Phys. Data |
|---|---|---|---|---|
| 1-7 | CH$_3$ | SCF$_3$ | OH | 19F: −45.9 −63.5 |
| 2-7 | CH$_3$ | SOCF$_3$ | OH | |
| 3-7 | CH$_3$ | SO$_2$CF$_3$ | OH | |
| 4-7 | CH$_3$ | SCClF$_2$ | OH | 19F: −30.4 −63.7 |
| 5-7 | CH$_3$ | SOCClF$_2$ | OH | |
| 6-7 | CH$_3$ | SO$_2$CClF$_2$ | OH | |
| 7-7 | CH$_3$ | SCCl$_2$F | OH | |
| 8-7 | CH$_3$ | SOCCl$_2$F | OH | |
| 9-7 | CH$_3$ | SC$_2$F$_5$ | OH | |
| 10-7 | CH$_3$ | SC$_2$H$_5$ | OH | |
| 11-7 | CH$_3$ | SCF$_3$ | OMe | |
| 12-7 | CH$_3$ | SCF$_3$ | OEt | |
| 13-7 | CH$_3$ | SMe | | |
| 14-7 | C$_2$H$_5$ | SCF$_3$ | OH | |
| 15-7 | CF$_3$ | SCF$_3$ | OH | |
| 16-7 | CHF$_2$ | SCF$_3$ | OH | |
| 17-7 | CF$_3$ | SOCF$_3$ | OH | |
| 18-7 | CF$_3$ | SO$_2$CF$_3$ | OH | |
| 19-7 | CF$_3$ | SCClF$_2$ | OH | |
| 20-7 | CF$_3$ | SCCl$_2$F | OH | |

TABLE 5

Compounds of formula (I) wherein $R_{202}$ is $SO_hR_{203}$; $R_{211}$ is Cl, $X_1$ is C—Cl, $R_{214}$ is H and $R_{213}$ is $CF_3$;
Phys. data: melting point (° C.) or NMR ($^1$H, $^{19}$F-NMR, ppm)

| Compound No | $R_{201}$ | $R_{202}$ | $R_{204}$ | Phys. data |
|---|---|---|---|---|
| 1-8 | CONH$_2$ | SCF$_3$ | OH | mp. 197 |
| 2-8 | CONH$_2$ | SOCF$_3$ | OH | |

TABLE 5-continued

Compounds of formula (I) wherein $R_{202}$ is $SO_hR_{203}$;
$R_{211}$ is Cl, $X_1$ is C—Cl, $R_{214}$
is H and $R_{213}$ is $CF_3$;
Phys. data: melting point (° C.) or NMR ($^1$H, $^{19}$F-NMR, ppm)

| Compound No | $R_{201}$ | $R_{202}$ | $R_{204}$ | Phys. data |
|---|---|---|---|---|
| 3-8 | $CONH_2$ | $SO_2CF_3$ | OH | |
| 4-8 | $CSNH_2$ | $SCF_3$ | OH | mp. 150 |
| 5-8 | $CSNH_2$ | $SOCF_3$ | OH | |
| 6-8 | $CSNH_2$ | $SO_2CF_3$ | OH | |
| 7-8 | $CONMe_2$ | $SCF_3$ | OH | |
| 8-8 | $C(NOH)NH_2$ | $SCClF_2$ | OH | mp. 156 |
| 9-8 | $C(NOH)NH_2$ | $SCF_3$ | OH | mp. 184 |
| 10-8 | $COCH_3$ | $SCF_3$ | OH | 19F: −44.5 −61.7 |
| 11-8 | $COCH_3$ | $SCClF_2$ | OH | 19F: −29.4 −61.0 |
| 12-8 | $CONH_2$ | $SCF_3$ | OEt | |
| 13-8 | $CONH_2$ | $SCClF_2$ | OEt | |
| 14-8 | Oxadiazolin-3-yl | $SCF_3$ | OH | |
| 15-8 | Oxazolin-2-yl | $SCF_3$ | OH | |
| 16-8 | $CON=S(iPr_2)$ | $SCF_3$ | OH | |
| 17-8 | $CON=S(iPr)_2$ | $SOCF_3$ | OH | |
| 18-8 | $CON=S(iPr)_2$ | $SO2CF_3$ | OH | |
| 19-8 | $CONH_2$ | $SCF_3$ | OMe | mp. 148–151 |

TABLE 6

Compounds of formula (I) wherein $R_{201}$ is CN;
$R_{202}$ is $SO_hR_{203}$; $R_{211}$ is Cl, $X_1$ is
C—Cl, $R_{214}$ is H and $R_{213}$ is $CF_3$;
Phys. data: melting point (° C.) or NMR ($^1$H, $^{19}$F-NMR, ppm)

| Compound No | $R_{202}$ | $R_{204}$ | Phys. data |
|---|---|---|---|
| 1-9 | $SCClF_2$ | OH | 19F: −30.7 −63.7 |
| 2-9 | $SOCClF_2$ | OH | |
| 3-9 | $SO_2CClF_2$ | OH | |
| 4-9 | $SCCl_2F$ | OH | |
| 5-9 | $SOCCl_2F$ | OH | |
| 6-9 | $SO_2CCl_2F$ | OH | |
| 7-9 | $SC_2F_5$ | OH | |
| 8-9 | $SCH_2CF_3$ | OH | |
| 9-9 | $SCCl_2CF_3$ | OH | |
| 10-9 | $SCCl_2CH_3$ | OH | |
| 11-9 | $SC_2H_5$ | OH | 1H: 1.25, 3H; 2.71, 3H; 7.72, 2H; |
| 12-9 | $SCHF_2$ | OH | |
| 13-9 | $SCClF_2$ | OEt | mp. 91 |
| 14-9 | $SOCClF_2$ | OEt | mp. 161 |
| 15-9 | $SCClF_2$ | $OCONMe_2$ | |
| 16-9 | $SCClF_2$ | OCOtBu | |
| 17-9 | $SCH_3$ | OH | mp. 66 |
| 18-9 | $SCH_3$ | $OCONMe_2$ | 1H: 2.43, 3H; 2.96, 6H; 7.75, 2H; |
| 19-9 | $SCBrF_2$ | OH | |
| 20-9 | $SCCl_3$ | OH | |
| 21-9 | $SCCl_2F$ | OMe | mp. 154 |
| 22-9 | $SOCCl_2F$ | OMe | mp. 136 |

TABLE 6-continued

Compounds of formula (I) wherein $R_{201}$ is CN;
$R_{202}$ is $SO_hR_{203}$; $R_{211}$ is Cl, $X_1$ is
C—Cl, $R_{214}$ is H and $R_{213}$ is $CF_3$;
Phys. data: melting point (° C.) or NMR ($^1$H, $^{19}$F-NMR, ppm)

| Compound No | $R_{202}$ | $R_{204}$ | Phys. data |
|---|---|---|---|
| 23-9 | $SO_2CCl_2F$ | OMe | mp. 189 |
| 24-9 | $SO_2CClF_2$ | OEt | mp. 130 |
| 25-9 | $SCClF_2$ | OMe | mp. 87 |
| 26-9 | $SOCClF_2$ | OMe | mp. 139 |
| 27-9 | $SO_2CClF_2$ | OMe | mp. 166 |

TABLE 7

Compounds of formula (I) wherein $R_{201}$ is CN;
$R_{202}$ is $SO_hR_{203}$; $R_{211}$ is Cl, $X_1$ is
C—Cl, $R_{214}$ is H and $R_{213}$ is $CF_3$;
Phys. data: melting point (° C.) or NMR ($^1$H, $^{19}$F-NMR, ppm)

| Compound No | $R_{202}$ | $R_{204}$ | Phys. data |
|---|---|---|---|
| 1-10 | $SCF_3$ | $OCH_2$—CCH | 19F: −44.6 −63.8 |
| 2-10 | $SCF_3$ | $OCH_2COOEt$ | mp. 71 |
| 3-10 | $SCF_3$ | OCOtBu | mp. 82 |
| 4-10 | $SCF_3$ | OCO-Ph-4-OMe | 19F: −43.5 −63.9 |
| 5-10 | $SCF_3$ | $OSO_2Me$ | mp. 110 |
| 6-10 | $SCF_3$ | OCO-Pyrrolidin | mp. 101 |
| 7-10 | $SCF_3$ | OCO-Morpholin | 19F: −43.5 −63.8 |
| 8-10 | $SCF_3$ | $OCO—N(i-Pr)_2$ | mp. 120 |
| 9-10 | $SCF_3$ | $OCO-NPh_2$ | mp. 142 |
| 10-10 | $SCF_3$ | OCO-N(Me)Ph | 19F: −43.6 −63.7 |
| 11-10 | $SCF_3$ | OCO-Carbazol | mp. 148 |
| 12-10 | $SCF_3$ | OCO-Adamantyl | mp. 142 |
| 13-10 | $SCF_3$ | OCO-Mesityl | mp. 103 |
| 14-10 | $SCF_3$ | $OCH_2Ph$ | mp. 73 |
| 15-10 | $SCF_3$ | $OSO_2$-4-Tolyl | |
| 16-10 | $SCF_3$ | $O—C(NMe)NMe_2$ | |
| 17-10 | $SCF_3$ | $O—CH=NC_2H_4OEt$ | |
| 18-10 | $SCF_3$ | $OCH_2CONH_2$ | mp. 156 |
| 19-10 | $SCF_3$ | $O—C(N(i-Pr))NHiPr$ | |
| 20-10 | $SCF_3$ | O—C(S)-NHEt | |

TABLE 8

Compounds of formula (I) wherein $R_{211}$ is Cl,
$X_1$ is C—Cl, $R_{214}$ is H and $R_{213}$ is $CF_3$;
Phys. data: melting point (° C.) or NMR ($^1$H, $^{19}$F-NMR, ppm)

| Compound No | $R_{201}$ | $R_{202}$ | $R_{204}$ | Phys. data |
|---|---|---|---|---|
| 1-11 | CN | 4,5-Dicyanoimidazol-2-yl | OH | |
| 2-11 | CN | 4,5-Dicyanoimidazol-2-yl | OEt | |
| 3-11 | $CH_3$ | 4,5-Dicyanoimidazol-2-yl | OH | |

TABLE 8-continued

Compounds of formula (I) wherein $R_{211}$ is Cl,
$X_1$ is C—Cl, $R_{214}$ is H and $R_{213}$ is $CF_3$;
Phys. data: melting point (° C.) or NMR ($^1$H, $^{19}$F-NMR, ppm)

| Compound No | $R_{201}$ | $R_{202}$ | $R_{204}$ | Phys. data |
|---|---|---|---|---|
| 4-11 | $CH_3$ | 4,5-Dicyanoimidazol-2-yl | OEt | 1H: 1.28, 3H; 2.55, 3H; 4.08, 2H; 7.77, 2H; |
| 5-11 | CN | —CH=$CCl_2$ | OEt | |
| 6-11 | CN | —$CH_2$CH=$CH_2$ | OAllyl | mp. 62–66 |
| 7-11 | CN | —CH=$CBr_2$ | OEt | |
| 8-11 | CN | Cyclopropyl | OEt | |
| 9-11 | CN | c-$C_6H_{11}$ | OEt | |
| 10-11 | CN | $NO_2$ | OH | mp. 107 |
| 11-11 | CN | $NO_2$ | OEt | |
| 12-11 | CN | —CC—Me | OEt | |
| 13-11 | CN | —CC—$SiMe_3$ | OEt | |

TABLE 9

Compounds of formula (I) wherein $R_{201}$ is CN;
$R_{202}$ is $SO_hR_{203}$; $R_{211}$ is Cl, $R_{214}$
and $R_{213}$ form the unit $CF_2OCF_2$;
Phys. data: melting point (° C.) or
NMR ($^1$H, $^{19}$F-NMR, ppm)

| Compound No | $R_{202}$ | $R_{204}$ | X = $CR_{212}$ | Phys. data |
|---|---|---|---|---|
| 1-12 | $SCF_3$ | OH | CH | |
| 2-12 | $SCF_3$ | OH | C—Cl | |
| 3-12 | $SCF_3$ | OEt | C—Cl | |
| 4-12 | $SOCF_3$ | OH | CH | |
| 5-12 | $SOCF_3$ | OH | C—Cl | |
| 6-12 | $SO_2CF_3$ | OH | CH | |
| 7-12 | $SO_2CF_3$ | OH | C—Cl | |
| 8-12 | $SCClF_2$ | OH | C—Cl | |
| 9-12 | $SCCl_2F$ | OH | C—Cl | |
| 10-12 | $SC_2H_5$ | OH | C—Cl | |

TABLE 10

Compounds of formula (I) wherein $R_{201}$ is CN;
$R_{202}$ is $SO_hR_{203}$; $R_{211}$ is Cl, $X_1$ is
C—Cl, $R_{214}$ is H and $R_{213}$ is $OCF_3$;
Phys. data: melting point (° C.) or NMR ($^1$H,
$^{19}$F-NMR, ppm)

| Compound No | $R_{202}$ | $R_{204}$ | Phys data |
|---|---|---|---|
| 1-13 | $SCF_3$ | OH | |
| 2-13 | $SOCF_3$ | OH | |
| 3-13 | $SO_2CF_3$ | OH | |
| 4-13 | $SCF_3$ | OMe | mp. 101 |
| 5-13 | $SOCF_3$ | OMe | mp. 104 |
| 6-13 | $SO_2CF_3$ | OMe | mp. 117 |
| 7-13 | $SCCl_2F$ | OMe | mp. 123 |
| 8-13 | $SCF_3$ | OEt | |
| 9-13 | $SOCF_3$ | OEt | |
| 10-13 | $SO_2CF_3$ | OEt | |

METHODS OF SYNTHESIS

Method 1

The compounds of formula (I) and (II) with $R_{204}/R_{24}$=OH and $R_{22}$=$SR_{23}$ can be synthesized by reacting 5-hydroxy-pyrazoles with sulfenylchlorides with or without bases in organic solvents (see e.g. EP-A-295 117):

METHOD 2

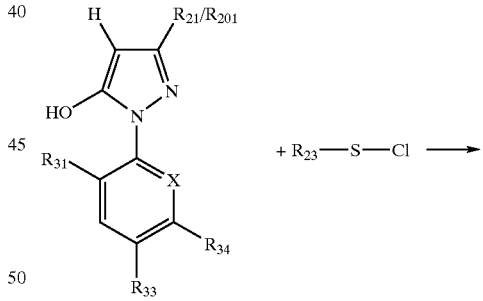

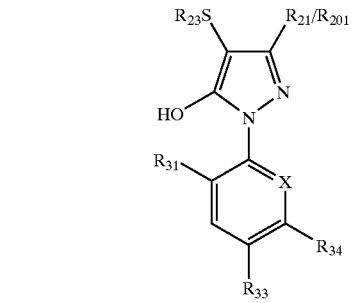

The compounds of formula (I) and (II) with $R_{204}/R_{24}$=OH and $R_{22}$=$SR_{23}$ can be synthesized by reacting 5-hydroxypyrazoles with disulfur dichloride. The resulting pyrazole-disulfides can be alkylated to yield 4-pyrazolsulfides (see e.g., EP-A-374 061, EP295117, C. Wakselman, *J. Chem. Soc. Perkin Trans* 1, 1992, 3371–3375):

METHOD 3

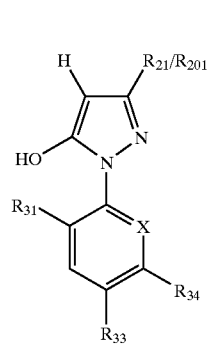

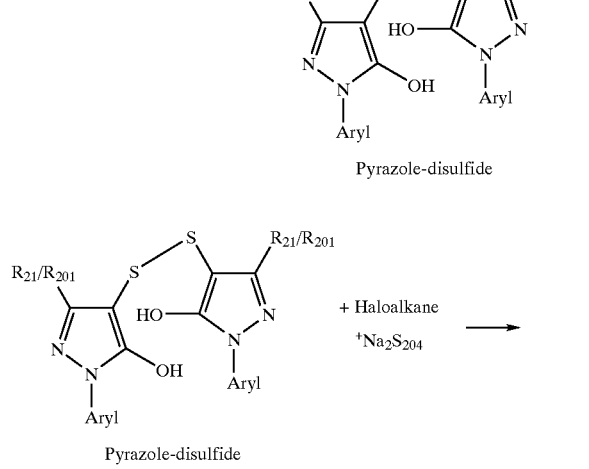

Pyrazole-disulfide

Haloalkane = CF$_3$BR, CFCl$_3$ a.o.

The compounds of formula (I) and (II) with R$_{204}$/R$_{24}$=OH and R$_{22}$=S(O)$_a$R$_{23}$ (a=1,2) can be synthesized by reacting pyrazolsulfides R$_{22}$=SR$_{23}$ with oxidizing agents like peroxy compounds (hydrogen peroxide, organic peroxides as peroxyacetic acid), halogen derivatives (like periodate salts) and others to obtain sulfoxides R$_{22}$=SOR$_{23}$ and sulfones R$_{22}$=SO$_2$R$_{23}$ (see e.g. EP-A-295 117).

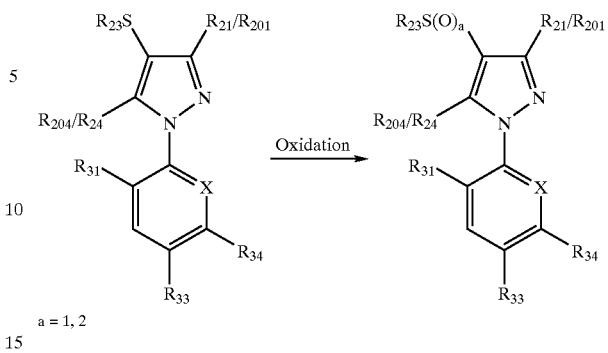

a = 1, 2

In another aspect of the present invention, compounds of formula (II) wherein R$_{24}$ is HC(O)O—, R$_{25}$C(O)O—, R$_{25}$OC(O)O—, or R$_{25}$S(O)$_n$C(O)O and R$_{21}$, R$_{22}$, R$_{31}$, R$_{33}$, X and n are defined above are generally prepared by reaction of compounds of formula (II) wherein R$_{24}$ is OH and R$_{21}$, R$_{22}$, R$_{31}$, R$_{33}$, X and n are defined above with compounds of formulae (III), (IV), (V), and (VI) respectively wherein X$_2$ is a leaving group such as a halogen atom or an acetyl group:

$$HC(O)X_2 \quad (III)$$

$$R_{25}C(O)X_2 \quad (IV)$$

$$R_{25}OC(O)X_2 \quad (V)$$

$$R_{25}S(O)_nC(O)X_2 \quad (VI)$$

Compounds of general formula (II) wherein R$_{24}$ is OH and R$_{21}$, R$_{22}$, R$_{31}$, R$_{33}$, X and n are defined above may be prepared by methods known in the art generally or by methods described in International Patent Publications WO 94/21606, WO 97/07102, WO 98/24767, WO 98/28277, WO 98/28278 and WO 98/28279, European Patent Application 385809, and U.S. Pat. No. 5,232,940, 5,047,550 or other methods known to the person skilled in the art.

The present invention also relates to a composition comprising a parasiticidally effective, substantially non-emetic amount of a compound of formula (I) or a salt thereof and an acceptable carrier. Acceptable carriers for the use of the compounds are generally known to the skilled addressee concerned with pest control in animals, particularly domestic animals, most preferably dogs or cats.

The compositions which can be used in the invention can comprise generally from about 0.001 to 95% of the compound of formula (I) or a salt thereof. The remainder of the composition up to 100% comprises a carrier as well as generally various additives. In this specification and the accompanying claims, percentages are by weight.

The diluted liquid formulations generally comprise from about 0.001 to about 3% of compound of formula (I) or a salt thereof, preferably from about 0.1 to about 0.5%.

Solid formulations generally comprise from about 0.1 to about 8% of compound of formula (I) or a salt thereof, preferably from about 0.5 to about 1.5%.

Compositions for oral administration comprise one or more of the compounds of general formula (I) or salts thereof in association with veterinarily acceptable carriers or coatings and include, for example, tablets, pills, capsules, gels, drenches, medicated feeds, medicated drinking water, medicated dietary supplements, slow-release boluses or other slow-release devices intended to be retained within the gastro-intestinal tract. Any of these may incorporate the active ingredients contained within micro-capsules or coated with acid-labile or alkali-labile or other pharmaceutically acceptable enteric coatings. Feed premixes or concentrates containing compounds of the present invention for use in preparation of medicated diets, drinking water or other materials for consumption by animals may also be used. In a highly preferred embodiment, the compositions are administered postprandially, preferably from just after a meal to 2 hours after the meal.

In a highly preferred embodiment, there is provided a product which is readily chewed by the animal and which product does generally not allow human contamination when the product is provided to the animal by hand.

The compounds of general formula (I) or salts thereof may be administered before, during or after meals. The compounds of general formula (I) or salts thereof may be mixed with a carrier and/or a foodstuff.

According to the present invention the compound of formula (I) or a salt thereof is administered orally in a dose to the animal in a dose range generally from 0.1 to 500 mg/kg of the compound of formula (I) or a salt thereof per kilogram of animal body weight (mg/kg), preferably from 1 to 100 mg/kg, more preferably from 1 to 50 mg/kg, even more preferably from 2 to 25 mg/kg, most preferably from 3 to 15 mg/kg.

According to the present invention, the frequency of treatment of the animal, preferably the domestic animal to be treated by the compound of formula (I) or a salt thereof is generally from about once per week to about once per year, preferably from about once every two weeks to about once every six months, more preferably from about once every two weeks to once every three months, and most preferably from about once every two weeks to about once every six weeks.

Generally the animal to be treated is a domestic animal, preferably a domestic companion animal. More preferably the animal to be treated is a dog and/or a cat.

Accordingly, in a preferred embodiment there is provided a method of controlling parasites in or on a cat comprising administering orally to the cat a parasitically effective, substantially non emetic amount of a 1-arylpyrazole of formula (I).

In a further preferred embodiment there is provided a method of controlling parasites in or on a dog comprising administering orally to the dog a parasitically effective, substantially non emetic amount of a 1-arylpyrazole of formula (I).

The present invention also relates to a composition comprising a parasiticidally effective amount of a compound of formula (II) or a salt thereof and an acceptable carrier. Acceptable carriers for the use of the compounds are generally known to the skilled addressee concerned with pest control in animals, particularly domestic animals, most preferably dogs or cats.

In another aspect of the present invention, the compounds of formula (II) or salts thereof may be used in the field of veterinary medicine or livestock husbandry or in the maintenance of public health against arthropods, helminths or protozoa which are parasitic internally or externally upon vertebrates, particularly warm-blooded vertebrates, for example domestic animals, e.g., cattle, sheep, goats, equines, swine, poultry, dogs or cats.

The compounds are administered to animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems.

Solid or liquid compositions for application topically to animals, timber, stored products or household goods usually contain from about 0.00005% to about 90%, more particularly from about 0.001% to about 10%, by weight of one or more compounds of formula (II) or veterinarily acceptable salts thereof. For administration to animals orally or parenterally, including percutaneously, in solid or liquid compositions, these normally contain from about 0.1% to about 90% by weight of one or more compounds of formula (II) or veterinarily acceptable salts thereof. Medicated feedstuffs normally contain from about 0.001% to about 3% by weight of one or more compounds of formula (II) or veterinarily acceptable salts thereof. Concentrates or supplements for mixing with feedstuffs normally contain from about 5% to about 90%, preferably from about 5% to about 50%, by weight of one or more compounds of formula (II) or veterinarily acceptable salts thereof. Mineral salt licks normally contain from about 0.1% to about 10% by weight of one or more compounds of formula (II) or veterinarily acceptable salts thereof.

Dusts or liquid compositions for application to livestock, goods, premises or outdoor areas may contain from about 0.0001% to about 15%, more especially from about 0.005% to about 2.0%, by weight, of one or more compounds of formula (II) or veterinarily acceptable salts thereof. Suitable concentrations in treated waters are between about 0.0001 ppm and about 20 ppm, more particularly about 0.001 ppm to about 5.0 ppm. of one or more compounds of formula (II), or veterinarily acceptable salts thereof, and may be used therapeutically in fish farming with appropriate exposure times. Edible baits may contain from about 0.01% to about 5%, preferably from about 0.01% to about 1.0%, by weight, of one or more compounds of formula (II) or veterinarily acceptable salts thereof.

When administered to vertebrates parenterally, orally or by percutaneous or other means, the dosage of compounds of formula (II), or veterinarily acceptable salts thereof, will depend upon the species, age, or health of the vertebrate and upon the nature and degree of its actual or potential infestation by arthropod, helminth or protozoan pests. A single dose of about 0.1 to about 500, preferably from 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The compounds of the invention may be administered most advantageously with another parasiticidally effective material, such as an endoparasiticide, and/or an ectoparasiticide, and/or an endectoparasiticide. For example, such compounds include macrocyclic lactones such as avermectins or milbemycins e.g., ivermectin; pyratel (generally adminsitered as pyrantel pamoate) or an insect growth regulator such as lufenuron or methoprene.

By the term "parasites" as used in the specification and claims is meant endoparasites and ectoparasites of warm-blooded animals, particularly ectoparasites. Preferably, fleas and/or ticks are controlled by the method of the present invention.

Illustrative of specific parasites of various host animals which may be controlled by the methods of this invention include arthropods such as:

Mites: *Mesostigmata* spp. e.g., mesostigmatids such as the chicken mite, *Dermanyssus gallinae*; itch or scab mites such as Sarcoptidae spp. for example *Sarcoptes scabiei*; mange mites such as Psoroptidae spp. including *Chorioptes bovis* and *Psoroptes ovis*; chiggers e.g., Trombiculidae spp. for example the north american chigger, *Trombicula alfreddugesi*;

Ticks: e.g., soft-bodied ticks including Argasidae spp. for example *Argas* spp. and *Ornithodoros* spp; hard-bodied ticks including Ixodidae spp., for example *Rhipicephalus sanguineus*, and *Boophilus* spp.;

Lice: sucking lice, e.g., *Menopon* spp. and *Bovicola* spp.; biting lice, e.g., *Haematopinus* spp., *Linognathus* spp. and *Solenopotes* spp.;

Fleas: e.g., *Ctenocephalides* spp., such as dog flea (*Ctenocephalides canis*) and cat flea (*Ctenocephalides felis*); *Xenopsylla* spp. such as oriental rat flea [*Xenopsylla cheopis*]; and *Pulex* spp. such as human flea [*Pulex irritans*];

True bugs: e.g., Cimicidae or including the common bed bug (*Cimex lectularius*);, Triatominae spp. including triatomid bugs also known as kissing bugs; for example *Rhodnius prolixus* and *Triatoma* spp.;

bloodsucking adult flies: (e.g., horn fly [*Haematobia irritans*], horse fly [*Tabanus* spp.], stable fly [*Stomoxys calcitrans*], black fly [*Simulium* spp.], deer fly [*Chrysops* spp.], louse fly [*Melophagus ovinus*], tsetse fly [*Glossina* spp.], mosquitoes [*Culex* spp., *Anopheles* spp., and *Aedes* spp.); and parasitic fly maggots: (e.g., bot fly [*Oestrus ovis* and *Cuterebra* spp.], blow fly [*Phaenicia* spp.], screwworm [*Cochliomyia hominivorax*], cattle grub [*Hypoderma* spp.], fleeceworm.

The present invention also provides for the use of a compound of formula (I) or a salt thereof hereinbefore described as a therapeutic agent, preferably for animals, more preferably for domestic animals.

The veterinary composition may be sterile or non-sterile. It may be a liquid (e.g., aqueous) or solid (e.g., dry) composition, in particular a freeze-dried composition, from which, by addition of water or another liquid, orally effective solutions may be prepared.

The present invention also provides for the use of a compound of formula (I) or a salt thereof as hereinbefore defined for the manufacture of a veterinary composition for the control of parasites in or on an animal.

In a further embodiment of the invention there is provided the use of a compound of formula (I) or salt thereof for controlling parasites in or on an animal without causing emesis of the animal.

Preferred is the use for orally administering the compound to the animal, which is preferably a domestic animal, highly preferred a cat or a dog.

In a further embodiment of the invention there is provided the use of a compound of formula (I) or salt thereof for the manufacture of a substantially non-emetic composition, for controlling parasites in or on an animal, preferably for oral administering.

The present invention also relates to a method of cleaning animals in good health comprising the application to the animal of a compound of formula (I) or a salt thereof as hereinbefore defined to the animal.

The method of cleaning an animal is not a method of treatment by therapy of the animal body per se, because (a) the animal is in good health and requires no substantial treatment to correct a deficiency of health;

(b) the cleaning of the animal is not intended to be done by veterinary personnel, but by persons interested in the cleaning of the animal; and (c) the purpose of such cleaning is to avoid unpleasant conditions for humans and the environment in which humans inhabit so as to not infest the said humans with arthropods carried by the animal.

By "carrier" is meant an organic or inorganic material, which can be natural or synthetic, and which is associated with the compound and which facilitates its application to the animal. This carrier is thus generally inert and should be arthropodicidally acceptable. The carrier can be solid (e.g., clay, silicates, silica, resins, wax) or liquid (e.g., water, alcohols, ketones, oil solvents, polar aprotic solvents). An example of an oil solvent is corn oil. An example of a polar aprotic solvent is dimethyl sulfoxide.

The compounds of the invention also have utility in the control of arthropod or nematode pests of plants. The active compound is generally applied to the locus in which arthropod or nematode infestation is to be controlled at a rate of about 0.005 kg to about 25 kg of active compound per hectare of locus treated, preferably 0.02 to 2 kg/ha. Under ideal conditions, depending on the pest to be controlled, the lower rate may offer adequate protection. On the other hand, adverse weather conditions, resistance of the pest and other factors may require that the active ingredient be used in higher proportions. For foliar application, a rate of 0.01 to 1 kg/ha may be used.

When the pest is soil-borne, the formulation containing the active compound is distributed evenly over the area to be treated in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulation can, if desired, be distributed mechanically in the soil, for example by ploughing or disking. Application can be prior to planting, at planting, after planting but before sprouting has taken place or after sprouting.

The compounds of the invention may be applied in solid or liquid compositions to the soil principally to control those nematodes dwelling therein but also to the foliage principally to control those nematodes attacking the aerial parts of the plants (e.g., *aphelenchoides* spp. and *ditylenchus* spp. listed above).

The compounds of the invention are of value in controlling pests which feed on parts of the plant remote from the point of application, e.g., leaf feeding insects are killed by the subject compounds applied to roots. In addition the compounds may reduce attacks on the plant by means of antifeeding or repellent effects.

The compounds of the invention are of particular value in the protection of field, forage, plantation, glasshouse, orchard and vineyard crops, or ornamentals and of plantation and forest trees, for example, cereals (such as maize, wheat, rice, sorghum), cotton, tobacco, vegetables and salads (such as beans, cole crops, curcurbits, lettuce, onions, tomatoes and peppers), field crops (such as potato, sugar beet, ground nuts, soyabean, oil seed rape), sugar cane, grassland and forage (such as maize, sorghum, lucerne), plantations (such as of tea, coffee, cocoa, banana, oil palm, coconut, rubber, spices), orchards and groves (such as of stone and pip fruit, citrus, kiwifruit, avocado, mango, olives, and walnuts), vineyards, ornamental plants, flowers and shrubs under glass and in gardens and parks, forest trees (both deciduous and evergreen) in forests, plantations and nurseries.

They are also valuable in the protection of timber (standing, felled, converted, stored or structural) from attack by sawflies (e.g., urocerus) or beetles (e.g., scolytids, platypodids, lyctids, bostrychids, cerambycids, anobiids), or termites, for example, reticulitermes spp., heterotermes spp., coptotermes.

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g., as carpets or textiles) from moth and beetle attack; also stored meat and fish from beetle, mite and fly attack.

The disclosure in U.S. provisional application No. 60/168,658 from which this application claims priority is incorporated herein by reference.

The invention is further illustrated by the following examples, without limiting it thereto.

EXAMPLES AND PREPARATIONS

Example 1

Preparation of 1-(2,6-Dichloro-4-trifluoromethylphenyl)-3-cyano-4-trifluoromethylsulfinyl-5-hydroxypyrazole To a solution of 15 g (35.5 mmol) of 1-(2,6-dichloro-4-trifluoromethylphenyl)-3-cyano-4-trifluoromethylsulfenyl-5-hydroxypyrazole in 125 ml of dichloromethane at room temperature was added a solution of m-chloroperbenzoic acid (8.76 g, 70%, 35.5 mmol) in 375 ml of dichloromethane. The resulting solution was stirred at room temperature for 17 hr. It was then concentrated and triturated with ethyl acetate and heptane(1:2). Upon filtration a solid was obtained. This solid was dissolved in ethyl acetate and stirred with saturated sodium bicarbonate solution. The layers were separated and the aqueous layer was extracted three times with ethyl acetate. The combined organic layer was dried (magnesium sulfate) and concentrated. Upon chromatographic purification via silica gel column, a solid (5.7 g, 13.01 mol, 37%) was obtained as the desired product, mp 185–187d.

Example 2

Preparation of 1-(2,6-Dichloro-4-trifluoromethylphenyl)-3-cyano-4-trifluoromethylsulfonyl-5-hydroxypyrazole To the solution of 2 g (4.74 mmol) of 1-(2,6-dichloro-4-trifluoromethylphenyl)-3-cyano-4-trifluoromethylsulfenyl-5-hydroxypyrazole in 1,2-dichloroethane was added 1.83 ml (9.52 mmol, 35% in acetic acid) of peracetic acid at room temperature. The resulting solution was heated up to 60 C for 9 hr. It was then cooled and concentrated to give 2.05 g of residue. Upon chromatographic purification via silica gel column eluting with gradient solvent mixture (heptane/ethyl acetate), an oil (1.08 g, 2.38 mmol, 50.2% yield) was obtained as the desired product with 98% HPLC purity; F-NMR, –60.999 ppm (AR—$CF_3$), –79.893 ppm ($SO_2CF_3$). H-NMR, 8.18 ppm (s, 2H).

Example 3

Preparation of 1-(2,6-dichloro-4-trifluoromethylphenyl)-3-amido-4-trifluoromethylsulfenyl-5-hydroxypyrazole To the mixture of 1-(2,6-dichloro-4-trifluoromethylphenyl)-3-cyano-4-trifluoromethylsulfenyl-5-hydroxypyrazole (3.0 g, 7.13 mmol) and concentrated sulfuric acid (3 ml) was heated at 100 C for 3 hr. The reaction mixture was cooled and poured into ice-water. A solid was collected via filtration and was washed with water. It was then vacuum dried to obtain a solid (2.88 g, 6.56 mmol, 92% yield) with 98% HPLC purity, m. p. 197–198 C.

Example 4

Preparation of 1-(2,6-dichloro-4-trifluoromethylphenyl)-3-thioamido-4-trifluoromethylsulfenyl-5-hydroxypyrazole The mixture of 1-(2,6-dichloro-4-trifluoromethylphenyl)-3-amido-4-trifluoromethylsulfenyl-5-hydroxypyrazole (1 g, 2.28 mmol) and Lawesson's reagent (0.49 g, 1.21 mmol) in toluene was heated up to reflux for 4 hr. The reaction mixture turned into a solution during this time. This solution was then cooled, concentrated, and purified via chromatographic purification to provide a solid (0.283 g, 0.623 mmol, 27.3% yield) with 96% HPLC purity m. p. 150–151 decomp.

Example 5

Preparation of 1-(2,6-Dichloro-4-trifluoromethylphenyl)-3-oximicamido-4-trifluoromethylsulfenyl-5-hydroxypyrazole To the solution of 1-(2,6-dichloro-4-trifluoromethylphenyl)-3-cyano-4-trifluoromethylsulfenyl-5-hydroxypyrazole (3.0 g, 7.11 mmol) in 15 ml of methanol at room temperature was added hydroxyamine hydrochloride (0.59 g, 8.53 mmol) and triethylamine (0.94 g, 9.24 mmol). The resulting mixture was stirred at room temperature for a total of 48 hr with additional hydroxyamine hydrochloride (1.18 g, 17.06 mmol) and triethylamine (1.88 g, 18.5 mmol) added portionwise. The resulting reaction mixture was concentrated and then dissolved in ethyl acetate. The organic layer was washed with saturated ammonium chloride, water, dried (sodium sulfate), and concentrated to give a brown oil which solidified after standing, m. p. 184 C.

Example 6

Preparation of 1-(2,6-Dichloro-4-trifluoromethylphenyl)-3-cyano-4-trifluoromethylsulfenyl-5-trimethylacetoxypyrazole To the solution of 1-(2,6-dichloro-4-trifluoromethylphenyl)-3-cyano-4-trifluoromethylsulfenyl-5-hydroxypyrazole (7.00 g, 16.6 mmol) and pyridine (4.91 g, 62.1 mmol) in 1,2-dichloroethane at room temperature was added trimethylacetyl chloride (4.37 g, 36.2 mmol) dropwise. Ice bath was used to maintain the temperature of the reaction. After 20 hr at room temperature, the organic layer was washed five times with aqueous $KHSO_4$ till the aqueous solution was at pH 1. The organic layer was then dried ($MgSO_4$) and concentrated to give a solid residue. Upon chromatographic purification via silica gel column of the solid residue, after trituration with pentane, a off-white solid (2.403 g, 28.6% yield, 97.0% HPLC purity) was provided as the desired product, m. p. 82–83 C.

Example 7

Preparation of 1-(2,6-dichloro-4-trifluoromethylphenyl)-3-cyano-4-chlorodifluoromethylsulfenyl-5-hydroxypyrazole To the solution of 1-(2,6-dichloro-4-trifluoromethylphenyl)-3-cyano-5-hydroxypyrazole (12.0 g, 37.3 mmol.) and pyridine (3.25 g, 41.0 mmol) in dichloromethane at −50 to −60 C was added chlorodifluoromethanesulfenyl chloride (8.1 g, 46.6 mmol). The resulting solution was gradually warmed up to room temperature. After 20 hr, the organic layer was washed five times with water. It was then washed with brine and dried ($Na_2SO_4$) to provide an oil. Upon chromatographic purification of the oil, a total of 11.6 g (26.4 mmol., 71% yield) of the desired product with 97% HPLC purity was isolated. F-NMR: −30.05 ppm ($CClF_2$), −63.80 ppm ($ArCF_3$).

BIOLOGICAL EXAMPLE

The compounds 1-(2,6-dichloro-4-trifluoromethylphenyl)-3-cyano-4-triflluromethylthio-5-hydroxypyrazole, 1-(2,6-dichloro-4-trifluoromethylphenyl)-3-cyano-4-trifluoromethylsulfinyl-5-hydroxypyrazole and 1-(2,6-dichloro-4-trifluoromethylphenyl)-3-cyano-4-trifluoromethylsulfonyl-5-hydroxypyrazole are formulated as 30 mg/mL formulations in a 1:1 volume/volume solution of dimethyl sulfoxide and corn oil. Using this formulation, mixed breed dogs and cats are treated at a rate of 10 mg of the compound per kg (mg/kg)of body weight of the dog and 20 mg/kg of the cat treated. The animals are fasted for at least 8 hours prior to treatment, fed half of the daily ration immediately prior to treatment, then allowed access to the remainder of the daily ration immediately following treatment.

All dogs are infested with cat fleas (*Ctenocephalides felis*) and with ticks (*Rhipicephalus sanguineus*) 1 day prior to administration of the compound. Cats are only infested with fleas. The initial flea and tick counts are performed 1 day after the administration of the compounds. At 7, 14, 21 and 28 days after treatment the dogs are re-infested with ticks and 8, 15, 22 and 29 days after treatment the dogs and cats are re-infested with fleas. At 1, 9, 16, 23 and 30 days after treatment the control of fleas and ticks in treated dogs and cats is determined versus a group of infested dogs and cats which receive a placebo consisting of a 1:1 volume/volume solution of dimethyl sulfoxide and corn oil. To determine the efficacies of the compounds, the arthropods are combed from the animals and counted.

Satisfactory results are obtained for many of the above-mentioned compounds in any of the three areas of evaluation without any significant side-effect for a period ranging from eight to thirty days: control of flea on dog, control of tick on dog, and control of flea on cat. They are: 1-(2,6-dichloro-4-trifluoromethylphenyl)-3-cyano-4-trifluoromethylsulfenyl-5-trimethylacetoxypyrazole 3-10, 1-(2,6-dichloro-4-trifluoromethylphenyl)-3-cyano-4-trifluoromethylsulfenyl-5-ethoxypyrazole 3-1, 1-(2,6-dichloro-4-trifluoromethylphenyl)-3-cyano-4-chlorodifluoromethylsulfenyl-5-hydroxypyrazole 1-9, 1-(2,6-dichloro-4-trifluoromethylphenyl)-3-cyano-4-trifluoromethylsulfenyl-5-hydroxypyrazole 1-1, 1-(2,6-dichloro-4-trifluoromethylphenyl)-3-cyano-4-trifluoromethylsulfonyl-5-hydroxypyrazole 1-5, 1-(2,6-dichloro-4-trifluoromethylphenyl)-3-cyano-4-trifluoromethylsulfinyl-5-hydroxypyrazole 1-3, 1-(2,6-dichloro-4-trifluoromethylphenyl)-3-cyano-4-trifluormethylsulfonyl-5-N,N-dimethylcarbamyloxypyrazole 19-1.

What is claimed is:

1. A compound having the formula (II):

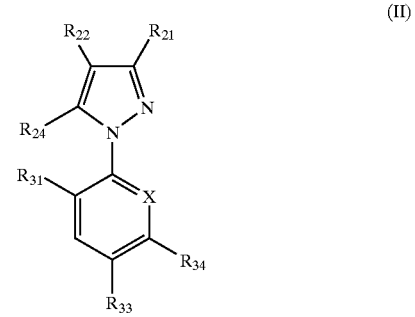

wherein:

$R_{21}$ is cyano, C(=S)$NH_2$, C(=NOH)$NH_2$ or C(=$NNH_2$)$NH_2$;

$R_{22}$ is S(O)$_m R_{23}$;

$R_{23}$ is alkyl or haloalkyl;

$R_{24}$ is OH, HC(O)O—, $R_{25}$C(O)O—, $R_{25}$OC(O)O—, $R_{25}R_{25}$N—C(O)—O— or $R_{25}$S(O)$_n$C(O)O—;

$R_{25}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, hetaryl optionally substituted, arylalkyl optionally substituted, hetarylalkyl optionally substituted, $C_2$–$C_6$ alkenyl or $C_2$–$C_6$ alkynyl;

or two groups $R_{25}$ form together with the nitrogen to which they are attached a 3 to 7 membered ring which optionally has one or more additional heteroatoms selected from the group consisting of nitrogen, oxygen and sulfur;

X is C—$R_{32}$;

$R_{31}$ and $R_{32}$ are independently selected from the group consisting of halogen, hydrogen, CN, $C_1$–$C_3$ alkyl and $NO_2$;

$R_{33}$ is selected from the group consisting of halogen, haloalkyl, haloalkoxy, —S(O)$_r CF_3$ and $SF_5$;

r is selected from the group consisting of 0, 1 and 2; and when $R_{21}$ is cyano, m is selected from the group consisting of 1 and 2, or when $R_{21}$ is other than cyano, m is selected from the group consisting of 0, 1 and 2;

or a veterinarily acceptable salt thereof;

provided that when $R_{21}$ is cyano, then $R_{24}$ is not $R_{25}R_{25}$—N—C(O)—O—.

2. A compound according to claim 1, wherein:

$R_{21}$ is cyano;

$R_{22}$ is S(O)$_m R_{23}$;

$R_{23}$ is haloalkyl;

$R_{24}$ is OH;

X is C—$R_{32}$;

$R_{31}$ and $R_{32}$ are independently selected from halogen;

$R_{33}$ is selected from the group consisting of halogen, haloalkyl, haloalkoxy, —S(O)$_r CF_3$, and —$SF_5$;

r is selected from the group consisting of 0, 1, and 2; and m is selected from the group consisting of 1 and 2.

3. A compound according to claim 2, wherein $R_{23}$ is $CF_3$.

4. The compound according to claim 2, which is 1-(2,6-dichloro-4-trifluoromethylphenyl)-3-cyano-4-trifluoromethylsulfinyl-5-hydroxypyrazole.

5. The compound according to claim 2, which is 1-(2,6-dichloro-4-trifluoromethylphenyl)-3-cyano-4-trifluoromethylsulfonyl-5-hydroxypyrazole.

6. A composition comprising a parasiticidally effective, substantially non-emetic amount of a compound of formula (II) as defined in claim 1, or a veterinarily acceptable salt thereof, and a veterinarily acceptable carrier therefor.

7. A composition comprising a parasiticidally effective, substantially non-emetic amount of a compound as defined in claim 2, and a veterinarily acceptable carrier therefor.

8. A composition comprising a parasiticidally effective, substantially non-emetic amount of a compound as defined in claim 3, and a veterinarily acceptable carrier therefor.

9. A composition comprising a parasiticidally effective, substantially non-emetic amount of a compound as defined in claim 4, and a veterinarily acceptable carrier therefor.

10. A composition comprising a parasiticidally effective substantially non-emetic amount of a compound as defined in claim 5, and a veterinarily acceptable carrier therefor.

11. A compound having the formula (II):

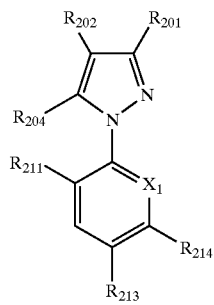

(I)

wherein:
$R_{21}$ is cyano, C(=S)NH$_2$, C(=NOH)NH$_2$ or C(=NNH$_2$)NH$_2$;
$R_{22}$ is S(O)$_m$R$_{23}$;
$R_{23}$ is alkyl or haloalkyl;
$R_{24}$ is OH, HC(O)O—, R$_{25}$C(O)O—, R$_{25}$OC(O)O—, R$_{25}$R$_{25}$N—C(O)—O— or R$_{25}$S(O)$_n$C(O)O—;
$R_{25}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, hetaryl optionally substituted, arylalkyl optionally substituted, hetarylalkyl optionally substituted, C$_2$–C$_6$ alkenyl or C$_2$–C$_6$ alkynyl;
or two groups $R_{25}$ form together with the nitrogen to which they are attached a 3 to 7 membered ring which optionally has one or more additional heteroatoms selected from the group consisting of nitrogen, oxygen and sulfur;
X is C—R$_{32}$;
$R_{31}$ and $R_{32}$ are independently selected from the group consisting of halogen, hydrogen, CN, C$_1$–C$_3$ alkyl and NO$_2$;
$R_{33}$ is selected from the group consisting of halogen, haloalkyl, haloalkoxy, —S(O)$_r$CF$_3$ and SF$_5$;
m is selected from the group consisting of 1 and 2; and
r is selected from the group consisting of 0, 1 and 2;
or a veterinarily acceptable salt thereof;
provided that when $R_{21}$ is cyano, then $R_{24}$ is not R$_{25}$R$_{25}$—N—C(O)—O—.

12. A compound having the formula (II):

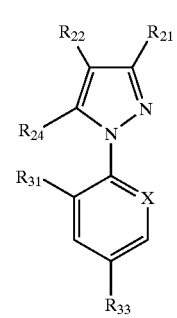

(II)

wherein:
$R_{21}$ is cyano;
$R_{22}$ is S(O)$_m$R$_{23}$;
$R_{23}$ is alkyl or haloalkyl;
$R_{24}$ is OH, HC(O)O—, R$_{25}$C(O)O—, R$_{25}$OC(O)O— or R$_{25}$S(O)$_n$C(O)O—;
$R_{25}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, hetaryl optionally substituted, arylalkyl optionally substituted, hetarylalkyl optionally substituted, C$_2$–C$_6$ alkenyl or C$_2$–C$_6$ alkynyl;
or two groups $R_{25}$ form together with the nitrogen to which they are attached a 3 to 7 membered ring which optionally has one or more additional heteroatoms selected from the group consisting of nitrogen, oxygen and sulfur;
X is C—R$_{32}$;
$R_{31}$ and $R_{32}$ are independently selected from the group consisting of halogen, hydrogen, CN, C$_1$–C$_3$ alkyl and NO$_2$;
$R_{33}$ is selected from the group consisting of halogen, haloalkyl, haloalkoxy, —S(O)$_r$CF$_3$ and SF$_5$;
m is selected from the group consisting of 1 and 2; and
r is selected from the group consisting of 0, 1 and 2;
or a veterinarily acceptable salt thereof.

13. A compound having the formula (II):

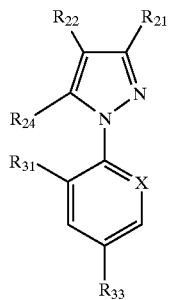

(II)

wherein:
$R_{21}$ is C(=S)NH$_2$, C(=NOH)NH$_2$ or C(=NNH$_2$)NH$_2$;
$R_{22}$ is S(O)$_m$R$_{23}$;
$R_{23}$ is alkyl or haloalkyl;
$R_{24}$ is OH, HC(O)O—, R$_{25}$C(O)O—, R$_{25}$OC(O)O— or R$_{25}$S(O)$_n$C(O)O— or R$_{25}$S(O)$_n$C(O)O—;
$R_{25}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, hetaryl optionally substituted, arylalkyl optionally substituted, hetarylalkyl optionally substituted, $C_2-C_6$ alkenyl or $C_2-C_6$ alkynyl;

or two groups $R_{25}$ form together with the nitrogen to which they are attached a 3 to 7 membered ring which optionally has one or more additional heteroatoms selected from the group consisting of nitrogen, oxygen and sulfur;

X is $C-R_{32}$;

$R_{31}$ and $R_{32}$ are independently selected from the group consisting of halogen, hydrogen, CN, $C_1-C_3$ alkyl and $NO_2$;

$R_{33}$ is selected from the group consisting of halogen, haloalkyl, haloalkoxy, $-S(O)_rCF_3$ and $SF_5$;

m is selected from the group consisting of 0, 1 and 2; and r is selected from the group consisting of 0, 1 and 2;

or a veterinarily acceptable salt thereof.

14. A composition comprising a parasiticidally effective, substantially non-emetic amount of a compound of formula (II) as defined in claim 11, or a veterinarily acceptable salt thereof, and a veterinarily acceptable carrier therefor.

15. A composition comprising a parasiticidally effective, substantially non-emetic amount of a compound as defined in claim 12, and a veterinarily acceptable carrier therefor.

16. A composition comprising a parasiticidally effective, substantially non-emetic amount of a compound as defined in claim 13, and a veterinarily acceptable carrier therefor.

17. A compound according to claim 1, having the formula (II):

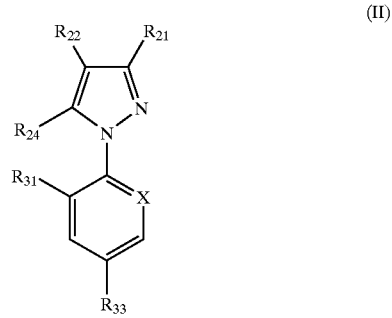

wherein:
$R_{21}$ is cyano, $C(=S)NH_2$, $C(=NOH)NH_2$ or $C(=NNH_2)NH_2$;
$R_{22}$ is $S(O)_mR_{23}$;
$R_{23}$ is alkyl or haloalkyl;
$R_{24}$ is OH, $HC(O)O-$, $R_{25}C(O)O-$, $R_{25}OC(O)O-$, $R_{25}R_{25}N-C(O)-O-$ or $R_{25}S(O)_nC(O)O-$;
$R_{25}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, arylalkyl optionally substituted, $C_2-C_6$ alkenyl or $C_2-C_6$ alkynyl;
X is $C-R_{32}$;
$R_{31}$ and $R_{32}$ are independently selected from the group consisting of halogen, hydrogen, CN, $C_1-C_3$ alkyl and $NO_2$;
$R_{33}$ is selected from the group consisting of halogen, haloalkyl, haloalkoxy, $-S(O)_rCF_3$ and $SF_5$;
r is selected from the group consisting of 0, 1 and 2; and
when $R_{21}$ is cyano, m is selected from the group consisting of 1 and 2, or
when $R_{21}$ is other than cyano, m is selected from the group consisting of 0, 1 and 2;
or a veterinarily acceptable salt thereof;

provided that when $R_{21}$ is cyano, then $R_{24}$ is not $R_{25}R_{25}-N-C(O)-O-$.

18. A compound according to claim 11, having the formula (II):

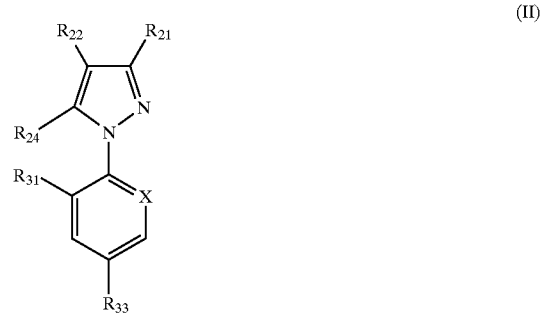

wherein:
$R_{21}$ is cyano, $C(=S)NH_2$, $C(=NOH)NH_2$ or $C(=NNH_2)NH_2$;
$R_{22}$ is $S(O)_mR_{23}$;
$R_{23}$ is alkyl or haloalkyl;
$R_{24}$ is OH, $HC(O)O-$, $R_{25}C(O)O-$, $R_{25}OC(O)O-$, $R_{25}R_{25}N-C(O)-O-$ or $R_{25}S(O)_nC(O)O-$;
$R_{25}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, arylalkyl optionally substituted, $C_2-C_6$ alkenyl or $C_2-C_6$ alkynyl;
X is $C-R_{32}$;
$R_{31}$ and $R_{32}$ are independently selected from the group consisting of halogen, hydrogen, CN, $C_1-C_3$ alkyl and $NO_2$;
$R_{33}$ is selected from the group consisting of halogen, haloalkyl, haloalkoxy, $-S(O)_rCF_3$ and $SF_5$;
m is selected from the group consisting of 1 and 2; and
r is selected from the group consisting of 0, 1 and 2;
or a veterinarily acceptable salt thereof;
provided that when $R_{21}$ is cyano, then $R_{24}$ is not $R_{25}R_{25}-N-C(O)-O-$.

19. A compound according to claim 12, having the formula (II):

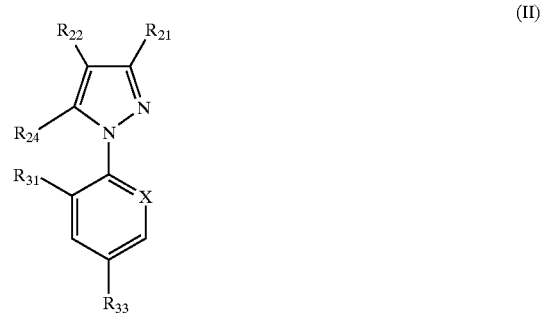

wherein:
$R_{21}$ is cyano;
$R_{22}$ is $S(O)_mR_{23}$;
$R_{23}$ is alkyl or haloalkyl;
$R_{24}$ is OH, $HC(O)O-$, $R_{25}C(O)O-$, $R_{25}OC(O)O-$ or $R_{25}S(O)_nC(O)O-$;
$R_{25}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, arylalkyl optionally substituted, $C_2$–$C_6$ alkenyl or $C_2$–$C_6$ alkynyl;

X is C—$R_{32}$;

$R_{31}$ and $R_{32}$ are independently selected from the group consisting of halogen, hydrogen, CN, $C_1$–$C_3$ alkyl and $NO_2$;

$R_{33}$ is selected from the group consisting of halogen, haloalkyl, haloalkoxy, —S(O)$_r$CF$_3$ and SF$_5$;

m is selected from the group consisting of 1 and 2; and r is selected from the group consisting of 0, 1 and 2;

or a veterinarily acceptable salt thereof.

20. A compound according to claim 13, having the formula (II):

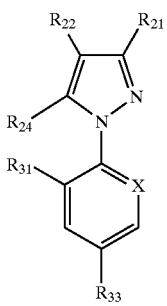

(II)

wherein:

$R_{21}$ is C(=S)NH$_2$, C(=NOH)NH$_2$ or C(=NNH$_2$)NH$_2$;

$R_{22}$ is S(O)$_m$R$_{23}$;

$R_{23}$ is alkyl or haloalkyl;

$R_{24}$ is OH, HC(O)O—, $R_{25}$C(O)O—, $R_{25}$OC(O)O—, $R_{25}$R$_{25}$N—C(O)—O— or $R_{25}$S(O)$_n$C(O)O—;

$R_{25}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, arylalkyl optionally substituted, $C_2$–$C_6$ alkenyl or $C_2$–$C_6$ alkynyl;

X is C—$R_{32}$;

$R_{31}$ and $R_{32}$ are independently selected from the group consisting of halogen, hydrogen, CN, $C_1$–$C_3$ alkyl and $NO_2$;

$R_{33}$ is selected from the group consisting of halogen, haloalkyl, haloalkoxy, —S(O)$_r$CF$_3$ and SF$_5$;

m is selected from the group consisting of 0, 1 and 2; and r is selected from the group consisting of 0, 1 and 2;

or a veterinarily acceptable salt thereof.

21. A compound according to claim 1, having the formula (II):

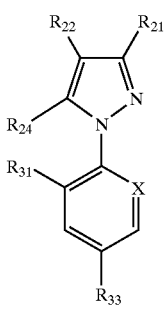

(II)

wherein:

$R_{21}$ is cyano, C(=S)NH$_2$, C(=NOH)NH$_2$ or C(=NNH$_2$)NH$_2$;

$R_{22}$ is S(O)$_m$R$_{23}$;

$R_{23}$ is alkyl or haloalkyl;

$R_{24}$ is OH;

$R_{25}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, arylalkyl optionally substituted, $C_2$–$C_6$ alkenyl or $C_2$–$C_6$ alkynyl;

X is C—$R_{32}$;

$R_{31}$ and $R_{32}$ are independently selected from the group consisting of halogen, hydrogen, CN, $C_1$–$C_3$ alkyl and $NO_2$;

$R_{33}$ is selected from the group consisting of halogen, haloalkyl, haloalkoxy, —S(O)$_r$CF$_3$ and SF$_5$;

r is selected from the group consisting of 0, 1 and 2; and when $R_{21}$ is cyano, m is selected from the group consisting of 1 and 2, or when $R_{21}$ is other than cyano, m is selected from the group consisting of 0, 1 and 2;

or a veterinarily acceptable salt thereof.

22. A compound according to claim 11, having the formula (II):

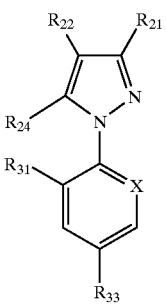

(II)

wherein:

$R_{21}$ is cyano, C(=S)NH$_2$, C(=NOH)NH$_2$ or C(=NNH$_2$)NH$_2$;

$R_{22}$ is S(O)$_m$R$_{23}$;

$R_{23}$ is alkyl or haloalkyl;

$R_{24}$ is OH;

$R_{25}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, arylalkyl optionally substituted, $C_2$–$C_6$ alkenyl or $C_2$–$C_6$ alkynyl;

X is C—$R_{32}$;

$R_{31}$ and $R_{32}$ are independently selected from the group consisting of halogen, hydrogen, CN, $C_1$–$C_3$ alkyl and $NO_2$;

$R_{33}$ is selected from the group consisting of halogen, haloalkyl, haloalkoxy, —S(O)$_r$CF$_3$ and SF$_5$;

m is selected from the group consisting of 1 and 2; and r is selected from the group consisting of 0, 1 and 2;

or a veterinarily acceptable salt thereof.

23. A compound according to claim 12, having the formula (II):

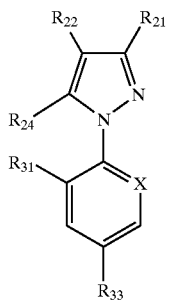

(II)

wherein:
R$_{21}$ is cyano;
R$_{22}$ is S(O)$_m$R$_{23}$;
R$_{23}$ is alkyl or haloalkyl;
R$_{24}$ is OH;
R$_{25}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, arylalkyl optionally substituted, C$_2$–C$_6$ alkenyl or C$_2$–C$_6$ alkynyl;
X is C—R$_{32}$;
R$_{31}$ and R$_{32}$ are independently selected from the group consisting of halogen, hydrogen, CN, C$_1$–C$_3$ alkyl and NO$_2$;
R$_{33}$ is selected from the group consisting of halogen, haloalkyl, haloalkoxy, —S(O)$_r$CF$_3$ and SF$_5$;
m is selected from the group consisting of 1 and 2; and
r is selected from the group consisting of 0, 1 and 2;
or a veterinarily acceptable salt thereof.

24. A compound according to claim 13, having the formula (II):

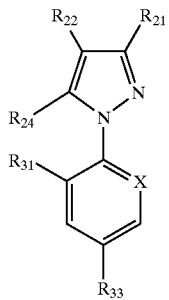

(II)

wherein:
R$_{21}$ is C(=S)NH$_2$, C(=NOH)NH$_2$ or C(=NNH$_2$)NH$_2$;
R$_{22}$ is S(O)$_m$R$_{23}$;
R$_{23}$ is alkyl or haloalkyl;
R$_{24}$ is OH;
R$_{25}$ is alkyl, haloalkyl, cycloalkyl, halocycloalkyl, alkoxyalkyl, haloalkoxyalkyl, adamantyl, aminoalkyl, alkylaminoalkyl, dialkylaminoalkyl, haloalkylaminoalkyl, di(haloalkyl)aminoalkyl, aryl optionally substituted, arylalkyl optionally substituted, C$_2$–C$_6$ alkenyl or C$_2$–C$_6$ alkynyl;
X is C—R$_{32}$;
R$_{31}$ and R$_{32}$ are independently selected from the group consisting of halogen, hydrogen, CN, C$_1$–C$_3$ alkyl and NO$_2$;
R$_{33}$ is selected from the group consisting of halogen, haloalkyl, haloalkoxy, —S(O)$_r$CF$_3$ and SF$_5$;
m is selected from the group consisting of 0, 1 and 2; and
r is selected from the group consisting of 0, 1 and 2;
or a veterinarily acceptable salt thereof.

25. A composition comprising a parasiticidally effective, substantially non-emetic amount of a compound of formula (II) as defined in claim 17, or a veterinarily acceptable salt thereof, and a veterinarily acceptable carrier therefor.

26. A composition comprising a parasiticidally effective, substantially non-emetic amount of a compound as defined in claim 18, and a veterinarily acceptable carrier therefor.

27. A composition comprising a parasiticidally effective, substantially non-emetic amount of a compound as defined in claim 19, and a veterinarily acceptable carrier therefor.

28. A composition comprising a parasiticidally effective, substantially non-emetic amount of a compound as defined in claim 20, and a veterinarily acceptable carrier therefor.

29. A composition comprising a parasiticidally effective, substantially non-emetic amount of a compound of formula (II) as defined in claim 21, or a veterinarily acceptable salt thereof, and a veterinarily acceptable carrier therefor.

30. A composition comprising a parasiticidally effective, substantially non-emetic amount of a compound as defined in claim 22, and a veterinarily acceptable carrier therefor.

31. A composition comprising a parasiticidally effective, substantially non-emetic amount of a compound of formula (II) as defined in claim 23, or a veterinarily acceptable salt thereof, and a veterinarily acceptable carrier therefor.

32. A composition comprising a parasiticidally effective, substantially non-emetic amount of a compound as defined in claim 24, and a veterinarily acceptable carrier therefor.

* * * * *

UNITED STATES PATENT AND TRADEMARK OFFICE
CERTIFICATE OF CORRECTION

PATENT NO. : 6,992,099 B2
APPLICATION NO. : 10/406491
DATED : January 31, 2006
INVENTOR(S) : Huber et al.

It is certified that error appears in the above-identified patent and that said Letters Patent is hereby corrected as shown below:

Column 22, lines 5 to 17, the portion of the formula reading "—$R_{34}$" should be deleted.

Column 23, lines 23 to 35, the formula should appear as follows:

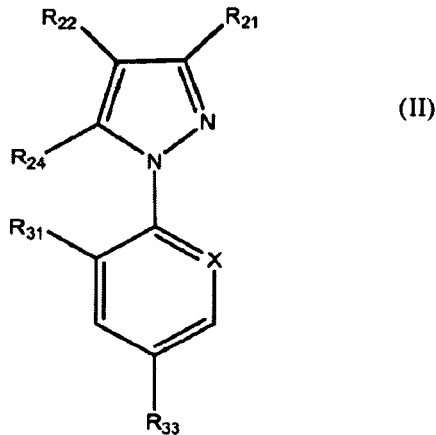

(II)

Column 22, line 44; Claim 11, column 23, line 64; Claim 12, column 23, line 41; Claim 13, column 25, line 16; Claim 17, column 25, line 62; Claim 18, column 26, line 39; Claim 19, column 27, line 11 and Claim 20, column 27, line 48; each occurrence of "r is" should be changed to --n and r are--.

Signed and Sealed this

Eighteenth Day of March, 2008

JON W. DUDAS
*Director of the United States Patent and Trademark Office*